United States Patent [19]

Schat et al.

[11] 4,160,024
[45] Jul. 3, 1979

[54] MAREK'S DISEASE VACCINE

[75] Inventors: Karel A. Schat; Bruce W. Calnek, both of Ithaca, N.Y.

[73] Assignee: Cornell Research Foundation, Inc., Ithaca, N.Y.

[21] Appl. No.: 901,635

[22] Filed: May 1, 1978

[51] Int. Cl.² ............................................. A61K 39/32
[52] U.S. Cl. ....................................... 424/89; 435/237
[58] Field of Search ............................. 424/89; 195/1.3

[56] References Cited

U.S. PATENT DOCUMENTS

| 3,642,574 | 2/1972 | Okazaki et al. | 424/89 X |
| 3,674,861 | 7/1972 | Churchill | 424/89 |
| 3,783,098 | 1/1974 | Calnek et al. | 195/1.1 |
| 3,981,771 | 9/1976 | Sevoian | 195/1.3 |

OTHER PUBLICATIONS

Calnek, et al. Avian Dis. 21(3):346-358, Sep. 1977, Pathogenicity of Low-virulence Marek's Disease Viruses in Normal Versus Immunologically Compromised Chickens.

Rispens et al., Avian Dis. 16(1):108-138 Apr. 1972, Control of Marek's Disease in the Netherlands I-II Isolation of an Avirulent Marek's Disease Virus (Strain CV1988).

*Primary Examiner*—Shep K. Rose
*Attorney, Agent, or Firm*—Jones, Tullar & Cooper

[57] ABSTRACT

A vaccine against Marek's disease is produced from a newly isolated Marek's disease virus which is unattenuated and naturally nononcogenic, even in immunosuppressed chickens.

8 Claims, No Drawings

MAREK'S DISEASE VACCINE

This invention is a subject invention of Public Health Service research granted No. 5 RO1 CA-06709-14 from the National Cancer Institute.

This invention relates to a novel method of immunizing chickens against Marek's disease (MD). More particularly, it relates to the production and use of a newly isolated Marek's disease virus, designated SB, and its cloned derivative, SB-1, for the immunization of chickens against Marek's disease, without thereby causing tumors in vaccinated chickens. The virus that is the subject of this invention is unattenuated and naturally nononcogenic, even in immunosuppressed or immunoincompetent chickens.

Marek's disease virus (MDV) is an oncogenic herpesvirus commonly found in chickens. Since isolates of MDV differ in the degree of pathogenicity, infection with MDV does not necessarily result in lymphoma formation or in the characteristic neural lesions generally associated with Marek's disease. Until now, unattenuated MD viruses have been unacceptable as vaccines for poultry because of the oncogenic potential even in viruses that are termed apathogenic. The only vaccine commercially available in the United States is the avirulent turkey herpesvirus (HVT) which is not an MDV but is antigenically related to MD viruses. The use of HVT as a vaccine was described by Witter, et al., Amer. J. Vet. Res. 31:524–538, 1970, and Okazaki, et al., Avian Diseases 14:413–429, 1970, and is implemented worldwide to immunize commercial flocks against MD. A serious disadvantage inheres in the use of HVT with commercial flocks. Chicks hatched from HVT immunized breeder chickens can resist vaccination with cell-free HVT, because maternal antibody against HVT is passed to the progeny through the egg, Calnek and Smith, Avian Diseases 16:954–957, 1972. That HVT immunized breeders pass on sufficient antibodies through the egg yolk to the chicks to interfere with vaccination with cell-free HVT is commercially important. The inability to optimally immunize chicks soon after hatching leaves some birds vulnerable to development of MD.

MDV antibody does not interfere with cell-free HVT vaccine. Thus, it is advantageous to be able to vaccinate breeders with an MD virus vaccine rather than the HVT vaccine, so the cell-free HVT vaccine can be used without interference in their progeny. Churchill, et al., J. Gen. Virol. 4:557–564, 1969, described a method of attenuating a virulent MDV and using the attenuated virus as a vaccine against MD in chickens. The method contemplates at least 32 passages in cell culture before the virus loses its oncogenicity. The virus that is the subject of the present invention does not require any artificial attenuation, and since it is in its natural state, cannot revert to a virulent form.

All MDV isolates carefully tested thus far have been considered to be oncogenic, although some are characterized by very low relative virulence. MD viruses, either attenuated or of naturally low virulence, were not considered to be suitable vaccines for use in commercial chickens because of this oncogenic potential or because of possible reversion to an oncogenic form. Smith and Calnek, Avian Pathol. 3:229–246, 1974, described the CU-2 isolate as being of low virulence, as CU-2 infected chickens evidenced no MD lymphomas but neural involvement was apparent. When CU-2 was tested in chickens that could not respond immunologically (immune response was suppressed surgically), it proved to be virulent and oncogenic. Rispens, et al., Avian Diseases 16:108–125, 1972; Ibid, Avian Diseases 16:126–138, 1972, described an MDV of low pathogenicity, designated CV1 988 strain. CV1 988 caused microscopic lesions in susceptible chicks, but became completely avirulent after further passages in cell culture. However, the strain was not tested for the presence of oncogenic potential in immunologically incompetent chickens. CV1 988, then, may be similar to CU-2. Another MDV with low pathogenicity, designated the HN isolate, was examined by Cho and Kenzy, Applied Microbiol. 24:199–306, 1972. The HN isolate induced a low incidence of lymphomas in highly susceptible chickens and thus is considered to be oncogenic. Similarly, Biggs and Milne, *Oncogenesis and Herpesvirus,* IARC, 1972, pp. 88–94, studied 25 MDV isolates, classifying the viruses according to pathogenicity. Several were labeled apathogenic, however, none were tested for oncogenicity in immunologically incompetent chickens. The virus described herein, SB and its cloned derivative, SB-1, does not possess the defect of potentially causing tumors in vaccinated chickens, as do the isolates previously described.

It is therefore the object of this invention to provide a vaccine for immunizing chickens against Marek's disease from a Marek's disease virus which is naturally nononcogenic, and thus does not have potential for causing tumors in vaccinated chickens.

This object and other features and advantages, are realized by inoculating the susceptible chickens with the SB strain of MDV, or its cloned derivative, SB-1. The original material used for the isolation of the SB virus was obtained from a flock of S-strain chickens, which are highly susceptible to MD. Hutt and Cole, Science 106:379–384, 1947. To prepare the vaccine, infected buffy coat cells were collected, then grown in chicken kidney culture (CKC). When the SB strain was isolated, it was passaged, and inoculated into susceptible chickens. Cell-free virus obtained from the skin of the infected birds was filtered and inoculated onto CKC. The SB-1 clone was selected from a terminal dilution and passed several times in CKC or chicken embryo fibroblasts (CEF). Vaccines thus produced are used to immunize chickens against Marek's disease by inoculating chicks prior to natural exposure to oncogenic strains of MDV. This is commonly done at one day of age.

Pathogenicity of SB-1 was evaluated in intact chickens and surgically immunosuppressed chickens by comparing the effect of SB-1 to other MDV isolates. Oncogenic potential is studied by the in ovo inoculation with SB of 8-day-old embryos. Protectivity was established by challenging chickens vaccinated at one and seven days of age with a highly oncogenic MDV isolate.

The MD resistant N-line and MD susceptible P-line chickens used in the experiments relative to this invention were described by Cole, Avian Diseases 12:9–28, 1968.

The viruses used to evaluate pathogenicity and protectivity of SB-1 have been described by Smith and Calnek, J. Natl. Cancer Inst. 52:1595–1603, 1974, and Calnek, J. Natl. Cancer Inst. 51:929–939, 1973. These included the high virulence MDV clones GA-5 and JM-10, the low virulence clone CU-2, and the HVT-4 clone of the HVT isolate FC-126. Apathogenic isolates HN-1, as described by Cho and Kenzy, Applied Microbiol. 24:229–306, 1972, and JS-1 and GM-1, as described by Cho and Kenzy, Infect. Immum. 11:804–814, 1975, were obtained from Richard Raymond (H&N Inc., Redmond, Wash.) and B. R. Cho (Washington State Univ.).

DETAILED DISCUSSION OF THE INVENTION

This invention relates to a method of immunizing chickens against Marek's disease without thereby causing tumors in vaccinated chicks comprising the step of inoculating susceptible chicks with nononcogenic unattenuated Marek's disease viruses known as SB or cloned derivatives thereof. In a preferred method the virus is prepared by a process which comprises the step of serially passing the nononcogenic virus through cell cultures to increase the virus titer to a useful level with the resultant virus constituting a vaccine characterized as an unattenuated nononcogenic Marek's disease virus. The preferred cell tissue cultures are chicken kidney and chicken embryo fibroblast cultures. Preferably chicks are inoculated shortly after hatching, or prior to exposure to oncogenic Marek's disease virus.

SB strain Marek's disease virus was obtained from whole blood of 28 week-old-S-strain chickens maintained by the Department of Poultry Science at Cornell University. The flock used had not been vaccinated against MD, yet had suffered no losses from MD at the time of sampling.

Buffy coat cells were collected and inoculated onto 24 hour old primary chicken kidney culture (CKC). After 13 days the SB strain could be distinguished by its characteristic plaque morphology. The cytopathic effects (CPE) seen differed from CPE induced by other MDV isolates in that foci in CKC induced by SB were generally unusually small although individual cells were enlarged; syncytia were common. Ordinarily, foci in CKC induced by virulent viruses are made up of clusters of rounded highly refractile cells. Similarly, in CEF inoculated with SB, CPE differed from that induced by typical virulent viruses in that numerous large plaques of rounded cells were seen, in contrast to a few small plaques caused in the former by an infection with GA-5. Culture cells infected with SB were passaged twice and then inoculated into susceptible one-day-old chicks. Cell-free virus was obtained 3 weeks later from the feather follicle epithelium in the skin of the main feather tracts of the infected birds.

The cell-free virus was filtered (0.3μ Millipore) and 2-fold dilutions were inoculated onto freshly prepared CKC. A clone was selected from a terminal dilution and identified as SB-1. The pathogenicity and protection experiments were conducted using either 6th passage uncloned SB or 11th passage SB-1. Viruses were stored as infected CKC or CEF at −196° C.

Using parallel titrations of different batches of SB or SB-1 on CKC and CEF it was found that the virus titers in CEF exceeded those in CKC by factors of 1.1 and 7.2. Thus, fewer than 11 passages may be employed, using CEF rather than CKC in order to reach an equivalent degree of multiplication. Two titrations of GA-5 were conducted in parallel cultures of CEF and CKC. In contrast to the above results, GA-5 titers were 100–200 times higher in CKC than in CEF, Table 1.

Table 1

Comparative titration of uncloned SB, and cloned SB-1 and GA-5 isolates of Marek's disease virus in chicken embryo fibroblast (CEF) and chick kidney cell (CKC) cultures.

| Virus | Passage level | Propagated in: | No. of focus forming units/ml[a] | |
|---|---|---|---|---|
| | | | CEF | CKC |
| SB | 4 | CKC | 8,900 | 6,200 |
| | 5 | CKC | 1,130 | 560 |
| | 5 | CKC | 18,200 | 5,600 |
| | 6 | CEF | 137,000 | 19,000 |
| SB-1 | 11 | CEF | 4,600 | 3,800 |
| | 11 | CEF | 3,850 | 3,400 |
| | 11 | CEF | 25,980 | 9,000 |
| GA-5 | 14 | CKC | 40 | 11,000 |
| | 14 | CKC | 50 | 4,700 |

[a]The number of focus forming units represents an estimate based on the mean count from duplicate assay cultures.

The results of agar gel precipitation (AGP) and immunofluourescent antibody (IFA) tests are summarized in Table 2.

Table 2

Serologic comparisons of the SB-1, JM-10, and CU-2, isolates of MDV and the FC-126 isolate of HVT.

| Virus | Isolate[a] | Test | Reciprocal titers of antisera | | | |
|---|---|---|---|---|---|---|
| | | | SB-1 | JM-10 | CU-2 | FC-126 |
| MDV | SB-1 | IFA | 2,560 | 640 | 640 | 160 |
| | | AGP | 4 | 0 | 0 | 0 |
| MDV | JM-10 | IFA | 160 | 1,280 | 2,560 | 80 |
| | | AGP | 2 | 4 | 4 | 0 |
| MDV | CU-2 | IFA | 320 | 1,280 | 1,280 | 80 |
| | | AGP | 2 | 4 | 4 | 2 |
| HVT | FC-126 | IFA | 160 | 160 | 320 | 1,280 |
| | | AGP | 2 | 2 | 2 | 8 |

[a]The apathogenic MDV isolates HN-1, GM-1, and JS-1 also were used as antigens in the IFA test; the results were comparable to those obtained with SB-1.

Hyperimmune sera against SB-1, JM-10, CU-2 and HVT were prepared in 7-week-old chickens which received two intravenous doses of infected CKC or CEF at a 3-week interval. One week after the second injection, the chickens were exsanguinated. Sera were separated and absorbed once with glutaraldehyde cross-linked bovine serum. Antigens for the AGP test were prepared in CKC using medium free of tryptose phosphate broth. Positive control sera were always placed in wells adjacent to test sera to enhance sensitivity and to determine specificity of the reactions. Antigens for the IFA test were cells grown on coverslips and infected with SB-1, HN-1, JS-1, GM-1, JM-10, CU-2 or HVT-4. The coverslips were harvested when CPE developed, fixed for 10 minutes in acetone at room temperature and stored at −20° C. Three groups were distinguished, based on comparative homologous and heterologous cross reactions: CU-2 and JM-10 were similar but different from SB-1; HVT was different from both MDV groups, Table 2. One way tests (results not shown) with the same antisera directed against 3 other apathogenic isolates (HN-1, GM-1, JS-1) yielded results similar to SB-1.

EXAMPLE 1

The pathogenicity of SB in intact chickens was evaluated by comparing 6th passage SB virus with 3 isolates representing high, low, and apathogenic MDV isolates: JM-10, CU-2, HN-1. Each virus was administered to twenty-five 7-day-old susceptible P-line chicks by injecting approximately 500 focus forming units (FFU) of infected CEF or CKC intra-abdominally (IA). Fifteen control chicks each received an equal number of uninfected CKC or CEF. At two weeks post infection (PI), 10 randomly selected birds from each of the infected and control groups were removed and sacrificed. The total body weights and the weights of the bursas of Fabricius were recorded. The bursas were then processed for histopathological examination. Damage to the bursa was assessed on the basis of relative weight, compared to that in the control chicks, and the number of follicles with severe damage. At six weeks PI, 10 infected birds from each infected group and 4 control chicks were examined for proliferative or degenerative gross lesions and histological lesions of MD. Degenerative lesions consisted of atrophy of thymus or bursa of Fabricius, or nephritis, or a combination of these changes. Tissues for histopathology included brain, proventriculus, liver, gonad, brachial and sciatic plexi, cervical vagus and celiac nerves.

The change in bursa weight and percentage of follicles with severe damage at 2 weeks PI are shown in Table 3. Neither SB nor HN-1 causes significant damage to the bursa of Fabricius, while both JM-10 and CU-2 induced considerable changes, reflected by a significant decrease in relative bursa weight. Histopathological examination revealed that JM-10 and CU-2 had altered a significant percentage of bursal follicles.

Table 3

Degenerative lesions in the bursae of Fabricius of P-line chickens exposed to various isolates of MDV at 7 days of age and held for 2 weeks (Experiment 1).

| Virus[a] | No. of chicks | Percent follicle damage[b] | Bursa wt/total body wt[c] Control group | Bursa wt/total body wt[c] Virus-infected group |
|---|---|---|---|---|
| JM-10 | 10 | 5.63 | 0.52±0.08 | 0.29±0.04[d] |
| CU-2 | 10 | 6.81 | 0.62±0.10 | 0.37±0.08[d] |
| HN-1 | 10 | 0 | 0.45±0.11 | 0.50±0.11 |
| SB | 10 | 0 | 0.61±0.13 | 0.59±0.11 |

[a]Each bird received an ia injection of 500 FFU infected CKC cells (JM-10 and CU-2) or CEF (HN-1 and SB). Controls received an equal number of uninfected cells.
[b]Percent of bursal follicles with severe depletion of lymphocytes, necrosis, or atrophy; at least 50 follicles/bird were evaluated.
[c]Mean of 10 birds±SD.
[d]Significantly different from control group at $p<0.001$.

Data on the incidence and character of MD at 6 weeks PI are summarized in Table 4. As expected, JM-10 was highly pathogenic. Upon gross examination, CU-2, HN-1 and SB were similar. However, the effect of CU-2 was shown to be markedly different from the effects of SB and HN-1, which were similar, upon histopathological examination. Chickens infected with CU-2 had a considerable number of lesions in the nerves, varying from heavy infiltrations of large lymphoblasts to infiltration of a few lymphocytes. Other organs, especially the brain and liver, also showed typical MD lesions. Chickens infected with HN-1 or SB were entirely free of microscopic lesions or had only very minimal nerve lesions consisting of a rare small area of infiltrations by small lymphocytes considered to represent inflammatory C-type lesions.

Table 4

Incidence of MD in P-line chickens exposed to low-virulence (SB, HN-1, and CU-2) or high-virulence (JM-10) isolates of MDV at 7 days of age and held for 6 weeks (Experiment 1).

| | | | No. of birds with MD | | | No. of birds with MD lesions[c] | | | | | | |
|---|---|---|---|---|---|---|---|---|---|---|---|---|
| | | | Survivors at 6 wk with | | | Gross lesions | | | Microscopic lesions | | | |
| Virus[a] | No. of birds | Dead[b] | Gross lesions | Microscopic lesions only | Total | Deg | NL | VL | Nerve | Conrad | Liver | Proventriculus | Brain |
| JM-10 | 10 | 4 | 4 | —[d] | 8 | 6 | 5 | 6 | —[d] | —[d] | —[d] | —[d] | —[d] |
| CU-2 | 10 | 0 | 1 | 6 | 7 | 0 | 0 | 1 | 5 | 1 | 5 | 2 | 6 |
| HN-1 | 10 | 0 | 0 | 2 | 2 | 0 | 0 | 0 | 1 | 0 | 0 | 0 | 1 |
| SB | 10 | 0 | 0 | 1 | 1 | 0 | 0 | 0 | 1 | 0 | 0 | 0 | 0 |

[a]Each bird received an ia injection of 500 FFU infected CKC cells (JM-10 and CU-2) or (HN-1 and SB).
[b]Dead = animals were MD-positive with one or more of the described lesions.
[c]Dog lesions = degenerative lesions of the bursa, thymus, and kidney; NL = Gross enlargement of peripheral nerves; VL = leukotic tumors in the visceral organs. The types of microscopic lesions are described in text. Chickens may be classified in more than one group.
[d]— = not tested.

EXAMPLE 2

15 S-strain and 14 P-line chicks were inoculated IA with 500 FFu of 11th passage SB-1 and kept for 11 weeks. Each chicken was examined for gross MD lesions and gonads and nerves of 8 S-strain chickens were examined histologically. No change in the pathogenicity of SB virus, compared to that seen in Example 1, was observed. No gross or microscopic lesions could be detected in either P-line or S-strain chickens.

EXAMPLE 3

The oncogenic potential of SB was evaluated by IA inoculation of 500 FFU in 7-day-old immuno-incompetent chicks. Surgical neonatal thymectomy (Tx) of S-strain and P-line embryos and bursectomy (Bx) of 17-day-old P-line embryos were performed during the seventeenth day of incubation. Tx and Bx chickens were examined postmortem for evidence of remnants of the respective organs. Functional evaluation of Tx was not done because previous studies had indicated that skin graft rejection or mitogen stimulation of peripheral blood lymphocytes did not correlate with the amount of thymus tissue left. Functional efficacy of Bx was evaluated following two intramuscular injections of 15 mg of bovine serum albumin (BSA) in 0.25 ml of phosphate buffered saline administered with a 14 day interval. One week after the second injection, serum was collected and tested for antibodies against BSA, using an indirect hemmagglutination test, and against MDV in an AGP test.

The effectiveness of Bx was almost 100%. One bird had a small bursa remnant and was therefore omitted from the results. The remaining 10 birds had no bursa remnants and failed to develop antibodies against BSA and MDV. In contrast, most of the hatchmates responded serologically to both BSA and MDV.

Based on the absence of grossly visible thymus lobes or remnants, Tx was complete in 62% of the P-line and 84% of the S-strain chickens. The remainder of the chickens had only one complete or incomplete lobe left. Table 5.

GA-5 infected CKC at 21 days of age. Dead birds and survivors were examined for the presence of degenerative lesions, gross neural involvement or visceral lym- Table 5

Incidence of MD after infection of immunosuppressed chicks with 500 FFU of passage 6 SB-infected CKC cells administered in ovo or 7 days after hatching

| Expt. No. | Age of infected host[b] | Treatment | Genetic strain | No. of birds | No. of birds with gross MD lesions[c] | | |
|---|---|---|---|---|---|---|---|
| | | | | | Only deg[c] | Nerve | Lymphous |
| 3 | 7-day chick | Tx | S-strain | 6 | 0 | 0 | 0 |
| | | Tx | P-line | 16 | 2 | 0 | 0 |
| | | Lx | P-line | 10 | 1 | 0 | 0 |
| 4 | 8-day embryo | None | P-line | 22 | 8[d] | 0 | 0 |
| | | None | N-line | 7 | 1 | 0 | 0 |
| | | Tx | N-line | 10 | 3 | 0 | 0 |

[a]Birds were held until 10 or 11 weeks of age.
[b]Embryonal inoculations were given via amnio-allantoic cavity. chick inoculations were given ia.
[c]Dog lesions = bureal arrophy, thymic arrophy, and nephritis. Nerve lesions = gross enlargement of the peripheral nerves.
[d]Three birds in this group died during the first 2–3 weeks as a result of acute necrotizing infection of the bursa of Fabricius, thymus, kidney, or other organs.

EXAMPLE 4

The oncogenic potential as SB was further evaluated by injection of 500 FFB into the amnio-allantoic cavity of 8-day-old P and N-line embryos. After hatching, half of the N-line chicks infected in ovo were Tx. These chicks were difficult to thymectomize. The thymus lobes were small and histology of thymus fragments which were removed revealed marked degeneration. Table 5.

None of treatments (Bx, Tx, in ovo inoculation, Tx combined with in ovo inoculation) in Examples 3 or 4 enhanced either the development of nerve lesions or visceral lymphomas. However, there was an increase in degenerative lesions, especially after in ovo inoculation (Table 5). It was concluded that SB can induce a lytic infection resulting in cell death and therefore degnerative lesions, but it reaches pathological levels only when the host is immunologically incompetent.

phomas. It was found that 500 FFU of SB protected the S-strain chickens against IA challenge with GA-5 at highly significant levels ($P < 0.005$), Table 6.

EXAMPLE 6

The experiment described in example 5 was performed on 7-day-old P-line chicks. 500 FFU of SB protected the P-line chickens at highly significant levels ($P < 0.01$), Table 6.

Example 7

1-day-old P-line chicks were vaccinated by IA inoculation of 100 FFU of SB or SB-1. Controls were established as in Examples 5 and 6. Viral challenge was performed by contact exposure to 3-week-old "shedders" of GA-5 MDV beginning at one day of age.

Inoculation with only 100 FFU of SB gave a highly significant level of protection against contact challenge on the day of vaccination ($P < 0.005$), Table 6.

Table 6

MD incidence in SB-vaccinated and control chickens challenged with the GA-5 isolate of MDV[a].

| Expt. no. | Genetic strain | Time and route of SB challenge[b] | Time and route of GA-5 challenge[c] | No. of birds with gross lesions[d] | | | | | No. of positive birds/total no. of birds |
|---|---|---|---|---|---|---|---|---|---|
| | | | | None | Only deg | Nerve only | Few small lymphomas | Massive lympomous | |
| 5 | S-strain | None | 21 days, ia | 3 | 0 | 0 | 0 | 17 | 12/15 |
| | | 7 days, ia | 21 days, ia | 11 | 0 | 0 | 0 | 2 | 2/13[e] |
| 6 | P-line | None | 21 days, ia | 4 | 0 | 0 | 0 | 10 | 10/14 |
| | | 7 days, ia | 21 days, ia | 10 | 0 | 0 | 0 | 2 | 2/12[f] |
| 7 | P-line | none | 1-day contact | 1 | 0 | 0 | 0 | 19 | 19/20 |
| | | 1 day, ia | 1-day contact | 25 | 8 | 1 | 6 | 9 | 25/49[e] |

[a]Birds were kept until 10 weeks of age
[b]SB was administered by ia inoculation of 500 FFU in experiments 5 and 6 and of 100 FFU in experiment 7. Controls received an equal number of uninfected CEF.
[c]GA=challenge was performed by ia inoculation of 150 FFU GA-5-infected CKC cells in experiments 5 and 6. Contact challenge in experiment 7 was done by the addition of lesions previously infected virus shedders at a 1:10 ratio of shedders to challenged chicks.
[d]Deg lesions = degenerative lesions of the buras of Fabricius, thymus, or kidneys. Nerve lesions = gross enlargement of the peripheral nerves. Massive visceral lymphomas or small and localized tumors often were accompanied by degeneration of the bursa and thymus.
[e]Difference in MD incidence between nonvaccinated and vaccinated groups was significant at the $P<0.005$ level ($X^2$ test).
[f]Difference in MD incidence between nonvaccinated and vaccinated groups was significant at the $P<0.01$ level ($X^2$ test).

EXAMPLE 5

The results of experiments to evaluate the protectivity of SB and SB-1 against MDV are summarized in the next 7 examples.

Seven-day-old S-strain chicks were vaccinated by IA inoculation of 500 FFU of SB or SB-1. Control chicks received a comparable number of uninfected CEF. Viral challenge was performed by IA inoculation of The lesion spectrum in vaccinated MD-positive chickens was different from that in the non-vaccinated birds. The non-vaccinated MD-positive chickens that died had massive visceral lymphomas, especially in the kidneys, as expected for the GA-5 infection. Only 9 of 24 vaccinated MD-positive chickens had typical GA-5 lesions, while 6 birds had only small localized tumors and degeneration of the lymphoid organs, and 8 had only degenerative lesions. Table 6.

EXAMPLE 8

Immune response was further evaluated by measuring protection afforded by SB-1 against JMV tumor cells. The JMV transplant was propagated from stocks originally obtained from Dr. M. Sevoian (Amherst, Mass.). Single cell suspensions of spleen of moribund chicks inoculated with JMV were used for the challenge inoculum. A positive response to JMV was signalled by mortality with enlarged spleens and livers. These experiments are summarized in the next 4 examples.

1-day-old P-line chickens were vaccinated by IA injection of SB-1 infected CEF containing 300 to 400 FFU. Challenge was made 14 days post-vaccination by IA inoculation of 1000 viable JMV cells. The results are shown in Table 7. SB-1 protected against the JMV challenge at highly significant levels (P <0.0005).

Table 7

Protection in SB-1 vaccinated chickens against challenge with the non-virus-producing MD tumor transplant JMV and Olson's TLT.

| Expt. No. | Strain of chicken | SB-1$^a$ | Challenge Tumor$^b$ | Days post vacci- nation | Specific mor- tality$^c$ | Level of signifi- cance ($X^2$ test) |
|---|---|---|---|---|---|---|
| 8$^d$ | P-line | + | JMV | 14 | 12/45 | P<0.005 |
|  |  | − | JMV | 14 | 39/46 |  |
| 9 | P-line | + | JMV | 7 | 2/20 | P<0.005 |
|  |  | − | JMV | 7 | 18/18 |  |
| 10 | N-line | + | JMV | 7 | 1/12 | P<0.0005 |
|  |  | − | JMV | 7 | 15/15 |  |
| 11 | N-line | + | TLT | 7 | 13/13 | Not significant |
|  |  | − | TLT | 7 | 12/13 |  |

$^a$SB-1 was administered to chickens at 1 day of age by ia injection of infected CEF containing between 300 and 400 FFU (+); the controls received an equal number of uninfected CEF (−). Birds were kept for 14-17 days post challenge.
$^b$JMV or TLT was given by inoculation of 1,000 viable cells ia or into the right pectoral muscle, respectively.
$^c$No. of positive birds/total no. of birds.
$^d$Pooled data of four trials with comparable results.

EXAMPLE 9

The experiment described in Example 8 was performed with challenge at 7 days post vaccination. The results are shown in Table 7.

EXAMPLE 10

The experiment described in Example 8 was performed on N-line chicks at 7 days post vaccination. The results are shown in Table 7.

EXAMPLE 11

Specificity of the protection was established by inoculation of 1000 viable culture cells of an avian leukosis tumor, the Olson transmissible lymphoid tumor transplant (TLT), in the right pectoral muscle of control and vaccinated N-line chicks at 7 days post vaccination. Positive response was indicated by progressive tumors in the pectoral muscle. Specificity of the protection against JMV was determined by the lack of protection in SB-1 vaccinated chickens against the TLT tumor cell challenge. Table 7.

While HN virus and SB virus share some properties, they are obviously different in the characteristic fundamental to the present teachings. Neonatal thymectomy prior to infection or in ovo infection result in infected chicks which are immunologically compromised and therefore the expression of low levels of oncogenicity is made possible. This was learned with low virulence strains of MDV like CU-1 and CU-2 (Avian Diseases 21:346-358, 1977). SB and SB-1 were tested by these methods and were nononcogenic. In contrast, HN virus caused a low incidence of neoplasms (lymphomas) even in intact (immunologically competent) chickens and the literature contains no reports that either HN or its clone, HN-1, have been tested under the rigorous conditions of Tx or in ovo infection which might expose low oncogenic potential. Therefore, unlike SB and SB-1, HN and HN-1 cannot be classified as nononcogenic.

Viruses SB and SB-1 are on deposit in the Department of Avian and Aquatic Animal Medicine, New York State College of Veterinary Medicine, Cornell University, Ithaca, N.Y. 14853 and are available to the public through that source.

We claim:

1. A method of immunizing chickens against Marek's disease without thereby causing tumors in vaccinated chicks comprising the step of inoculating susceptible chicks with a nononcogenic, unattenuated Marek's disease virus vaccine prepared in accordance with a process which comprises the step of serially passing nononcogenic SB strain of Marek's disease virus or a cloned derivative thereof through cell cultures to increase the virus titer to a useful level but without attenuating the original characteristics of the virus.

2. A method of immunizing chickens against Marek's disease without thereby causing tumors in vaccinated chicks comprising inoculating susceptible chicks with an unattenuated, nononcogenic Marek's disease virus vaccine prepared in accordance with a process which comprises the steps of:
   a. inoculating a cell culture selected from the group comprising chicken kidney and chicken embryo fibroblast cultures wiht the nononcogenic SB strain of Marek's disease virus or a cloned derivative thereof;
   b. serially passing the virus to increase virus titer to a useful level, but without attenuating the original characteristics of the virus;
   c. inoculating chicks with said resulting virus, the resulting virus constituting a vaccine against Marek's disease characterized as an unattenuated, nononcogenic, Marek's disease virus.

3. A method of immunizing chickens against Marek's disease without thereby causing tumors in vaccinated chicks comprising the step of inoculating susceptible chicks, with a nononcogenic, unattenuated Marek's disease virus, known as SB-1.

4. A method of immunizing chickens against Marek's disease without thereby causing tumors in vaccinated chicks comprising the step of inoculating susceptible chicks shortly after hatching, with a nononcogenic, unattenuated Marek's disease virus, known as SB-1.

5. A method of immunizing chickens against Marek's disease without thereby causing tumors in vaccinated chicks comprising the step of inoculating susceptible chicks with a naturally nononcogenic, unattenuated Marek's disease virus, known as SB.

6. A method of immunizing chickens against Marek's disease without thereby causing tumors in vaccinated chicks comprising the step of inoculating susceptible chicks, shortly after hatching, with a naturally nononcogenic, unattenuated Marek's disease virus, known as SB.

7. A method of immunizing chickens against Marek's disease without thereby causing tumors in vaccinated chicks comprising the step of inoculating susceptible chicks, prior to exposure to oncogenic Marek's disease virus, with a nononcogenic, unattenuated Marek's disease virus, known as SB-1.

8. A method of immunizing chickens against Marek's disease without thereby causing tumors in vaccinated chicks comprising the step of inoculating susceptible chicks, prior to exposure to oncogenic Marek's disease virus, with a naturally nononcogenic, unattenuated Marek's disease virus, known as SB.

* * * * *